United States Patent
Redel et al.

(10) Patent No.: US 10,245,001 B2
(45) Date of Patent: Apr. 2, 2019

(54) GENERATION OF A THREE-DIMENSIONAL RECONSTRUCTION OF A BODY PART BY AN X-RAY MACHINE

(71) Applicants: Thomas Redel, Poxdorf (DE); Michael Scheuering, Nürnberg (DE)

(72) Inventors: Thomas Redel, Poxdorf (DE); Michael Scheuering, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/614,838

(22) Filed: Jun. 6, 2017

(65) Prior Publication Data
US 2017/0347985 A1 Dec. 7, 2017

(30) Foreign Application Priority Data
Jun. 7, 2016 (DE) .................. 10 2016 210 003

(51) Int. Cl.
| A61B 6/02 | (2006.01) |
| A61B 6/00 | (2006.01) |
| A61B 6/08 | (2006.01) |
| A61B 6/04 | (2006.01) |

(52) U.S. Cl.
CPC .............. *A61B 6/5205* (2013.01); *A61B 6/08* (2013.01); *A61B 6/461* (2013.01); *A61B 6/504* (2013.01);
(Continued)

(58) Field of Classification Search
CPC .. A61B 6/02; A61B 6/022; A61B 6/52; A61B 6/5205; A61B 6/5235;
(Continued)

(56) References Cited

U.S. PATENT DOCUMENTS

| 2008/0014643 A1 | 1/2008 | Bjorkholm |
| 2008/0171936 A1 | 7/2008 | Homan et al. |

(Continued)

FOREIGN PATENT DOCUMENTS

| CN | 101150986 A | 3/2008 |
| CN | 102793552 A | 11/2012 |

(Continued)

OTHER PUBLICATIONS

European Search Report for related European Application No. 17170648.4 dated Aug. 2, 2017.
(Continued)

*Primary Examiner* — Thomas R Artman
(74) *Attorney, Agent, or Firm* — Lempia Summerfield Katz LLC

(57) ABSTRACT

The disclosure relates to an X-ray machine and a method for the operation of the X-ray machine for generation of a three-dimensional reconstruction of a body part. The method includes supplying a first X-ray capture of the body part; an automatic analysis of the first X-ray capture; an evaluation of the suitability of at least one further capture angle by the computing unit in the light of a result from the automatic analysis; setting of a second capture angle on the X-ray machine, either automatically by the computing unit or manually by an operator; a manually controlled approach to the set second capture angle by a capture unit of the X-ray machine; and capture of the second X-ray capture from the approached second capture angle by the capture unit to provide an improved method for operation of an X-ray machine for generation of a three-dimensional reconstruction of a body part.

15 Claims, 3 Drawing Sheets

(52) U.S. Cl.
CPC .............. *A61B 6/545* (2013.01); *A61B 6/027* (2013.01); *A61B 6/0457* (2013.01); *A61B 6/4441* (2013.01); *A61B 6/5294* (2013.01); *A61B 6/547* (2013.01)

(58) Field of Classification Search
CPC . A61B 6/5241; G06T 11/005; G06T 2200/08; G06T 2207/10081; G06T 2211/436
See application file for complete search history.

(56) References Cited

U.S. PATENT DOCUMENTS

| 2013/0266123 | A1 | 10/2013 | Yoshida et al. |
| 2013/0342851 | A1 | 12/2013 | Dresel et al. |
| 2014/0086384 | A1 | 3/2014 | Wei et al. |

FOREIGN PATENT DOCUMENTS

| CN | 103356218 A | 10/2013 |
| CN | 103445865 A | 12/2013 |
| DE | 102008034178 A1 | 2/2010 |
| WO | WO2016202881 A1 | 12/2016 |

OTHER PUBLICATIONS

Shengxian Tu et al: "In vivo assessment of bifurcation optimal viewing angles and bifurcation angles by three-dimensional (3D) quantitative coronary angiography", The International Journal of Cardiac Imaging, Kluwer Academic Publishers, DO, Bd. 28, Nr. 7; pp. 1617-1625, XP035125848, ISSN: 1573-0743, DOI: 10.1007/S10554-011-9996-X; 2011.
German Office Action for related German Application No. 10 2016 210 003.3 dated Feb. 9, 2017, with English Translation.
Chinese Office Action for Chinese Application No. 201710422662.1 dated May 8, 2018, with English Translation.

GENERATION OF A THREE-DIMENSIONAL RECONSTRUCTION OF A BODY PART BY AN X-RAY MACHINE

The application claims the benefit of German Patent Application No. DE 10 2016 210 003.3, filed Jun. 7, 2016, incorporated by reference in its entirety.

TECHNICAL FIELD

The disclosure relates to a method for the operation of an X-ray machine for the generation of a three-dimensional reconstruction of a body part. The disclosure also relates to an X-ray machine for the capture of at least two X-ray images for the generation of a three-dimensional reconstruction of a body part with a capture unit for the capture of X-ray captures from capture angles settable on the X-ray machine and approachable by the capture unit under manual control.

BACKGROUND

A three-dimensional model of a body part, (e.g., of a blood vessel, a portion of a blood vessel, and/or an organ), may be used in order to calculate a fractional flow reserve (FFR) value, the model being generated by angiography, e.g., using two X-ray captures captured at different angles. A capture or X-ray capture is also described as an acquisition or angiography scene. The data contained in a capture represent a film with a plurality of frames from a generally stationarily or invariably specified angulation, e.g., from a capture angle specified relative to the body part.

The model is subsequently generated from two captures or acquisitions. A suitable frame from each of the two captures is selected for this purpose. Based on these captures, a computer draws conclusions regarding the three-dimensional structure of the body part and generates a three-dimensional reconstruction of the body part as a 3D model. The body part may then be analyzed for the purposes of quantifying the fractional flow reserve. A resultant value as a numerical value for a diagnostic result of the body part is also denoted an angio-FFR value. In some examples, between 9 and 20 X-ray captures are captured to arrive at a diagnostic finding. The X-ray captures may also be captured for further intended uses, which means that angiography scenes or X-ray captures optimized for another use are or have to be used for the generation of the model. This limits the quality of the 3D model of the body part.

Alternatively, one or more additional captures may subsequently be taken for a three-dimensional reconstruction optimized for assessment in the context of a FFR analysis. This is a burden on the health of the patient or his/her body part. Whether the X-ray capture is taken subsequently or the X-ray captures already obtained are selected for the generation of the 3D model or three-dimensional reconstruction of the body part is today substantially determined by the individual experience of the X-ray machine operator, e.g., a doctor.

It is thus typically the case in the prior art that both X-ray captures are first captured, then saved and a three-dimensional model is subsequently generated from the existing X-ray captures that may thus no longer be influenced.

Another major disadvantage in existing systems and methods is that the saved X-ray captures may already have been optimized (e.g., post-processed) for visual examination. Therefore, the angio-FFR value may subsequently only be determined with reduced quality. The reason for this may be that the processing acts advantageous for visual examination complicate subsequent processing of a different nature, as is necessary for example for a densitometric assessment.

SUMMARY AND DESCRIPTION

The scope of the present disclosure is defined solely by the appended claims and is not affected to any degree by the statements within this description. The present embodiments may obviate one or more of the drawbacks or limitations in the related art.

The object arises of providing an improved method for the operation of an X-ray machine for the generation of a three-dimensional reconstruction of a body part. In particular, the three-dimensional reconstruction is intended to be suitable for calculating a fractional flow reserve value.

The disclosure relates to a method for the operation of an X-ray machine for the generation of a three-dimensional reconstruction of a body part, (e.g., a blood vessel, a portion of a blood vessel, and/or an organ). The method includes a series of acts that may be carried out in the stated sequence or alternatively in a different sequence. Individual acts may optionally also be carried out repeatedly.

One act is to supply a first X-ray capture of the body part, previously investigated or to be investigated, to a computing unit of the X-ray machine. The X-ray capture was captured from a first capture angle. The first X-ray capture may be a capture that was captured previously, (e.g., also for another purpose), and stored in a data system. The first X-ray capture may also have been captured before, (e.g., immediately before), supply by a capture unit of the X-ray machine.

A further act is automatic analysis of the supplied first X-ray capture by the computing unit. Automatic analysis may also include reading out a first capture angle of the first X-ray capture. The automatic analysis may also be complemented by manual analysis. The features of the automatic analysis stated further below may alternatively or additionally be carried out in the manual analysis. Automatic analysis may also include semi-automatic analysis, in which automatic analysis is possible only with the assistance of an operator, for example by user interaction such as selection of a specific region of the image. Automatic image preprocessing of the first and/or second X-ray capture, (for example, for quantitative analysis by an operator or doctor), may proceed in parallel to the automatic analysis.

Another act is an evaluation of the suitability of at least one further capture angle, (e.g., a plurality of further capture angles), for the generation of the three-dimensional reconstruction of the body part by the computing unit. This may also proceed based on the first capture angle. The computing unit thus evaluates the extent or degree to which one or more further capture angles are suitable for the generation of the three-dimensional reconstruction with the highest possible quality, for example with the highest possible accuracy. The computing unit takes account of at least one result from the automatic analysis. Evaluation may proceed based on specified criteria. The decisive factor is that a second X-ray capture from a second capture angle is captured or is to be captured for the generation of the three-dimensional reconstruction (subsequently, e.g., after evaluation). The second capture angle may then be the capture angle which was evaluated or one of the further capture angles which were evaluated.

A following act is setting the second capture angle on the X-ray machine. This may be carried out automatically by the computing unit, a result from the evaluation of the suitability of the second capture angle for the generation of the three-dimensional reconstruction being taken into account. Alternatively, this may be carried out manually by an operator, a result from the evaluation of the suitability of the second capture angle for the generation of the three-dimensional reconstruction being displayed to the operator by a display unit of the X-ray machine. This is followed by a manually controlled approach to the set second capture angle by a capture unit of the X-ray system as the next act and capture of the second X-ray capture from the approached second capture angle by the capture unit.

A further act may be an automatic analysis of the second X-ray capture by the computing unit. The analysis may correspond to the analysis of the first X-ray capture.

A further act may likewise be generation of the three-dimensional reconstruction of the body part from the two X-ray captures by the computing unit.

The method thus assists an operator, (e.g., a doctor), in obtaining data for the generation of the three-dimensional model from the outset, e.g., right from capture of the necessary X-ray captures on which the generation of the three-dimensional model is based. Improved quality of the resultant model, and thus in particular more accurate calculation of a fractional flow reserve value, is thus straightforwardly possible. The captured X-ray captures or X-ray images may also be repeatedly processed in parallel, namely on the one hand be displayed optimized for visual examination and on the other hand be displayed or saved or supplied to the computing unit in a version optimized for subsequent image processing or image assessment, (e.g., densitometric assessment).

The advantage is obtained that the operator is assisted by the system in setting or approaching the optimum second angulation, e.g., the optimum second capture angle for the generation of the three-dimensional model. It is thus the second X-ray capture that is capable of better and more rapidly supplying frames, which result in a more accurate three-dimensional reconstruction of the body part. The method is also less dependent on the experience or level of knowledge of the operator, so reducing variability in the quality of the X-ray captures and thus of the three-dimensional model and the calculations based on the model, (e.g., calculation of the fractional flow reserve value). The assessment is thus more reliable. Evaluation of suitability by the computing unit simultaneously also serves as a quality control, because objectively reproducible suitability criteria for the second capture angle are available.

In one advantageous embodiment, a further method act involves the operator selecting, from a plurality of intended purposes for captures by the X-ray machine, "generation of a three-dimensional reconstruction" on an operator control unit of the X-ray machine as the intended purpose for the first X-ray capture. Selection thus corresponds to selecting a specified option with at least one specified capture parameter setting for the X-ray capture from a plurality of specified options each having at least one further specified capture parameter setting for X-ray captures on the X-ray machine.

A further act includes setting the first capture angle for the first X-ray capture. The setting may be made both by the operator and by the computing unit. At least one further capture or acquisition parameter for the first X-ray capture is also automatically set by the computing unit. The capture parameter(s) may include one or more of: a capture angle, an intensity of the X-rays during capture, a position of the capture unit, an operating voltage of the capture unit, an operating current of the capture unit, or at least one parameter for image preprocessing that proceeds automatically.

A further act is manually controlled approach to the set first capture angle by the capture unit of the X-ray system and capturing the first X-ray capture from the approached first capture angle by the capture unit. The capture unit may be a mobile capture unit such as for example a C arm of an X-ray machine.

This has the advantage that the capture parameters most suitable for the intended application are automatically set and, as a result, the suitability of the first X-ray capture for the generation of the three-dimensional reconstruction is improved in a particularly simple manner. The quality of the three-dimensional reconstruction is thus again straightforwardly improved.

It may also be provided that selection also involves specifying the body or vessel part to be reconstructed. Setting of the first capture angle may be carried out automatically by the computing unit or manually by an operator, in the latter case, suitability of the set first capture angle for the generation of the three-dimensional reconstruction being displayed to the operator by the display unit of the X-ray machine based on the selected specification of the body part to be reconstructed. This may proceed in accordance with the features described further above for setting the second capture angle. In particular, at least one further capture parameter may also be set automatically. When automatically setting the first capture angle, a model of the body part to be reconstructed and/or the surroundings thereof in the body may be stored in the computing unit. Certain selections, (e.g., a capture angle that is advantageous due to a conventionally occurring blood vessel geometry), may thus be set. In certain examples, the angulations may be those at which the body part has fewer superposed structures, which result in unwanted shadows in the capture.

This has the advantage of further simplifying the method such that the doctor only need approach a specified angulation or a specified first capture angle or, during setting of the first capture angle, need only take note of an indication or recommendation from the computing unit. The method is again simplified and the quality and suitability of the first X-ray capture for the generation of the three-dimensional reconstruction are improved by appropriate selection of the first capture angle.

In a further advantageous embodiment, capture of the first and the second X-ray captures includes automatically varying the capture angle during capture by a few degrees around the set capture angle. In particular, the capture angle may be varied by less than 10 degrees, by less than 5 degrees, or by less than 2 degrees. This has the advantage that an overlapping vessel system or body part system may be examined from different, slightly different angles resulting in an improved chance of obtaining an image with no or fewer superposed structures in which the desired body part or vessel part is overlapped only slightly or not at all by any other body parts or vessel parts. Experience has shown that modifying the capture angle by a few degrees is sufficient to avoid such superposed structures that, for example, complicate automatic edge detection of vessels filled with contrast agents, if for example small vessels cross the vessel actually to be detected. However, because such a slight variation in capture angle in itself has virtually no influence on the generation of a three-dimensional image from two two-dimensional frames, the gain in quality in the three-dimensional reconstruction predominates overall. It is also possible in this way to avoid having to select another frame, (e.g., a frame to be assigned to a less favorable cardiac phase), during subsequent processing for the generation of the three-dimensional model. There is also, for example, no need for an operator to make an estimated correction. The accuracy, simplicity and reproducibility of the method are also again increased.

A further advantageous embodiment provides that the automatic analysis includes automatic detection of at least one region of the body part with specified characteristics such as a region of a blood vessel with a stenosis, and/or a position of the body part, e.g., a position of the body part on the X-ray capture in relation to a portion of the capture, e.g., a distance from an image center point or isocenter, and/or an orientation of the body part and/or at least one dimension of the body part, e.g., a geometric size sufficient for a fractional flow reserve, and/or a course of the body part and/or an axis of rotation, about which the second X-ray capture is optimally tilted relative to the first X-ray capture for the generation of the three-dimensional reconstruction of the body part. The axis of rotation may extend parallel to the image plane of the first X-ray capture. The axis of rotation may extend in the image plane of the first X-ray capture. The axis of rotation and the capture angle of the second X-ray capture may be optimally selected such that the image plane of the second X-ray capture is perpendicular to the image plane of the first X-ray capture and perpendicular to a course of the body part.

Automatic analysis may also include selection of a frame from the capture. For example, a frame may include a cardiac phase and/or a filling level of the body part with blood suitable for the intended purpose, in one example producing a three-dimensional reconstruction. Detection of the at least one region of the body part with the specified characteristics may be carried out in the computing unit for example via an edge detection and/or segmentation algorithm. Alternatively, detection may also be entirely or partially carried out or assisted by the operator. For example, a region of a body part having the specified characteristics may be input into the computing unit by an operation such as clicking on a region of the image or automatic analysis of further image areas may be assisted in this manner.

This also offers the advantage that selection of the second capture angle for the second X-ray capture for the generation of the three-dimensional reconstruction is automatically or semi-automatically improved in this manner. The accuracy and reliability of the three-dimensional reconstruction and, in particular, of the investigation of the functional flow reserve is thus increased.

A further embodiment provides that the specified criterion for evaluating the suitability of the capture angle includes one or more of the following criteria: an angular difference between the first capture angle and the at least one further capture angle, a probability of the X-ray machine, (e.g., the capture unit), colliding with further equipment (e.g., a patient table of the X-ray machine, the operator, and/or the patient), a patient dose burden in accordance with a patient or body part model stored in the computing unit, approachability of the capture angle, in particular from a current position of the capture unit, by the capture unit, a path length traveled by the X-rays in the patient and/or body part in accordance with a model of the patient or body part stored in the computing unit or a number or extent of further body parts superposed over the body part in the X-ray capture in accordance with a model of the body part and/or further body parts stored in the computing unit. Approachability may be evaluated based on a number of components to be moved for approaching the capture angle or a time required for approaching the capture angle.

Alternatively, an evaluation of suitability may also be estimated. In this case, once the body part to be reconstructed in three dimensions has been specified, one or more of the stated criteria may be estimated even without or with only very cursory analysis of the first X-ray capture. Estimation may be carried out based on a model stored in the computing unit. In particular, machine learning methods may also be applied here.

The stated criteria have the advantage that they have a particularly major impact on the quality of the three-dimensional reconstruction or achieve other desirable objectives such as maintaining the best possible patient health and/or the speed at which the capture angle may be reached by the capture unit.

A further advantageous embodiment provides that the evaluation of suitability for the specified criterion takes account of at least one minimum requirement and, in the event of the minimum requirement not being met by the evaluated capture angle, the computing unit prevents the evaluated capture angle being set as the second capture angle and/or warns the operator in the event of the evaluated capture angle being set as the second capture angle.

This has the advantage that the efficiency of the method is increased. Errors which might be made by the operator are detected at an early stage, so providing that the three-dimensional reconstruction is generated rapidly and unnecessary additional captures are avoided.

It may be provided that the minimum requirement includes a specified angular amount by which the first and second capture angles differ. In particular, the differential angle between the two captures arising from the first and second capture angles and by which the two capture angles differ, may amount to 20 degrees, 30 degrees, or 40 degrees. This has the advantage that the three-dimensional reconstruction does not fall below a specified minimum quality.

A further advantageous embodiment provides that the X-ray machine includes a patient table with an electrical adjustment function for the patient with the body part to be reconstructed in three dimensions. The adjustment function is disabled during capture of the first or second X-ray capture such that an operator may no longer adjust the patient table. In particular, in the period between the two X-ray captures either the adjustment function is disabled or adjustment of the patient table is detected by a detection unit and taken into account by the computing unit during setting of the second capture angle. In particular, disabling of the electrical adjustment function may be coupled to selecting "generation of a three-dimensional reconstruction" from a plurality of possible intended purposes, as is described above. This has the advantage that the spatial relationship of the two X-ray captures to one another, which is vital to the quality of the three-dimensional reconstruction, is defined and thus known during generation of the three-dimensional reconstruction. The accuracy of the three-dimensional reconstruction may thus straightforwardly be improved.

A further advantageous embodiment provides that, in the light of the results from the automatic analysis and/or evaluation of the suitability of the respective X-ray capture or captures for the generation of the three-dimensional reconstruction, the computing unit automatically preselects correlated frames or pairs of frames from the two X-ray captures. Frames of the different X-ray captures are, for example, correlated if they correspond to the same cardiac phase and/or the same filling level of the body part captured therein. This also gives rise to the advantage that the information already available and stored in the system is utilized to provide the operator with the best possible assistance and, independently or as independently as possible of the operator's level of knowledge, straightforwardly to obtain a high quality three-dimensional reconstruction of the body part.

It may furthermore also be provided to analyze the capture angles for the body part or vessel part or vessel segment retrospectively once the three-dimensional reconstruction of the body part has been generated from the two X-ray captures. This is possible because the position of the body part in relation to a position of the capture unit, (e.g., a C-arm), is of course known from the three-dimensional model. If, for example, due to curvatures in the body part, individual parts have been captured from an unfavorable angle, these regions, where the three-dimensional reconstruction is thus known to be of reduced accuracy, may be marked, (e.g., in color), so providing an indication of the possibly likewise reduced accuracy of the fractional flow reserve assessment in the region. This also serves to simplify carrying out quality control.

A further advantageous embodiment provides that, once the second X-ray capture has been captured, (e.g., once the three-dimensional reconstruction of the body part has been generated), an analysis of the second X-ray capture, (e.g., of the three-dimensional reconstruction), is carried out. The analysis may also be an automatic analysis. Furthermore, in this case too, an evaluation of the suitability of at least one further capture angle for the generation of an improved three-dimensional reconstruction of the body part is carried out by the computing unit. The evaluation is carried out in the light of a result from the analysis. In order to generate the improved three-dimensional reconstruction, a third X-ray capture is captured from a third capture angle and the acts of setting, manually controlled approach, and capture already known for the second X-ray capture are carried out for the third X-ray capture. Further of the acts known for the first and/or second X-ray capture(s) may optionally also be carried out for the third X-ray capture. In particular, it is possible to set a capture angle for the third X-ray capture which, combined with the first or with the second X-ray capture, allows generation of an optimum, e.g., best possible, three-dimensional reconstruction of the body part. An optimum combination of capture angles may be determined because the previous capture angles and, based on the model, also the course of the body part are known to the computing unit.

This has the advantage that an optimum capture angle may be set for the first retrospectively known actual position and orientation of the body part to be reconstructed and the best possible three-dimensional reconstruction may straightforwardly be generated.

The disclosure also relates to an X-ray machine for the capture of at least two X-ray images for the generation of a three-dimensional reconstruction of a body part. The X-ray machine includes a capture unit for the capture of X-ray captures from at least one, thus one or more, capture angle(s) settable on the X-ray machine and approachable by the capture unit under manual control. The X-ray machine further has a computing unit for the automatic analysis of at least one first X-ray capture, captured from a first capture angle, which is supplied to the computing unit. The computing unit is also designed for evaluating the suitability of at least one further capture angle or a plurality of further capture angles for the generation of the three-dimensional reconstruction of the body part in the light of a result from the automatic analysis. At least one second X-ray capture from at least one second capture angle may be captured by the capture unit for the generation of the three-dimensional reconstruction.

Advantages and advantageous embodiments of the X-ray machine correspond to the advantages and advantageous embodiments of the method for the operation of an X-ray machine for the generation of a three-dimensional reconstruction of a body part.

The features and combinations of features stated above in the description and the features and combinations of features stated below in the description of the figures and/or shown solely in the figures are usable not only in the respectively stated combination but also in other combinations without going beyond the scope of the disclosure. Embodiments that are not explicitly shown and explained in the figures but are apparent and may be produced from separated combinations of features based on the explained embodiments may also be considered. Embodiments and combinations of features which thus do not include all the features of an independent claim worded as filed may also be considered. Embodiments and combinations of features, in particular the above-stated embodiments, which extend beyond or deviate from the combinations of features defined in the back-references of the claims, may furthermore be considered.

BRIEF DESCRIPTION OF THE DRAWINGS

Exemplary embodiments are explained in greater detail below with reference to schematic drawings, in which.

In the figures, elements that are the same or have the same function are provided with the same reference signs.

DETAILED DESCRIPTION

Figure 1:
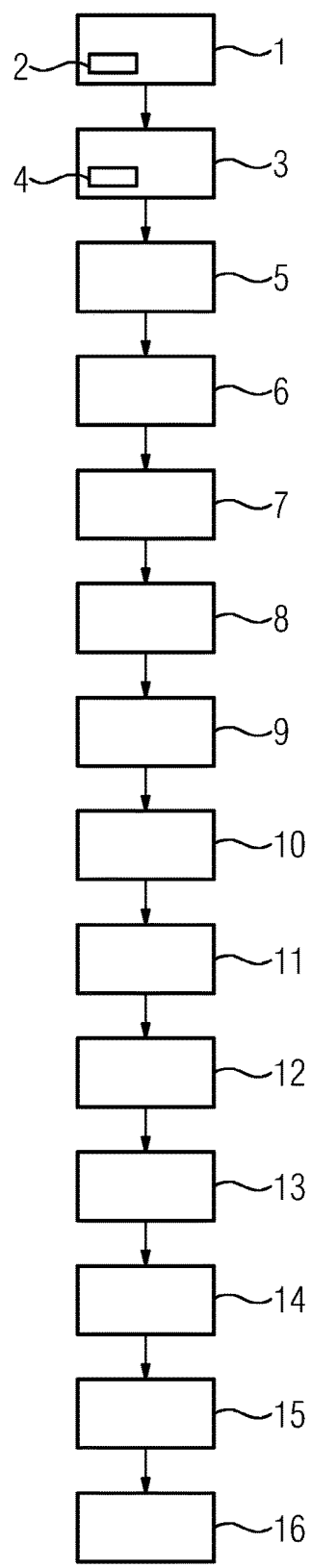
FIG. 1 depicts a flow chart of an exemplary method for the operation of an X-ray machine for the generation of a three-dimensional reconstruction of a body part.

FIG. 1 depicts a schematic diagram of a flow chart of an exemplary method for the operation of an X-ray machine for the generation of a three-dimensional reconstruction of a body part. In the present case, a first act involves an operator, (e.g., a doctor), selecting a specific capture program of the X-ray machine, namely "generation of a three-dimensional reconstruction". In the example shown, selection also includes specifying 2 the body part to be reconstructed. In the example shown, the doctor accordingly selects, from a plurality of possible intended purposes for captures by the X-ray machine, the option "generation of a three-dimensional reconstruction of a right coronary artery", for short for example "3D-model RCA", as the intended purpose.

In the example shown, the best capture or acquisition parameters for the generation of a three-dimensional reconstruction are automatically set 3 as a consequence. A radiation intensity may, for example, be set automatically. In the present case, automatic setting 3 of the capture parameter also includes automatic setting 4 of the first capture angle. In accordance with the selected body part, a suitable angulation, e.g., a suitable capture angle, is in the present case automatically set for the capture of the right coronary artery.

The doctor now only has to carry out the manually controlled approach 5 to the set first capture angle, whereupon the first X-ray capture is captured 6.

In the example shown, once the first X-ray capture has been supplied 7 to a computing unit, the first X-ray capture is analyzed 8 by the doctor. Analysis 8 in the present case includes selecting a frame with a suitable cardiac phase from the first X-ray capture. It further includes the doctor defining the stenosis, e.g., by clicking on or marking the examined vessel segment on a display unit of the X-ray machine, e.g., a screen. Analysis 8 by the doctor furthermore also includes checking whether the vessel segment, (e.g., the right-hand coronary artery), to be examined is detected without any superposition of other blood vessels or organs. If this is not the case, the doctor may correct the capture parameters and/or the first capture angle and optionally also carry out further acts.

In a following act, an automatic analysis 9 of the first X-ray capture is carried out by the computing unit. This includes, for example, edge detection and detection of the extent of the vessel to be examined or of the vessel segment with the stenosis. On this basis, it is possible to calculate a center line 23 (FIG. 2) that extends along the course of the vessel segment affected by the stenosis. A straight line may be approximated to this center line 23 as an axis of rotation 24 (FIG. 2) for the capture angle for the second X-ray capture.

If the center line 23 is strongly curved, the operator may be notified that the second capture angle cannot be entirely optimally set. In this case, the axis of rotation 24 may also be selected as a tangent to the center line 23 in the region of the stenosis. If the stenosis is very long and part of the curvature or the stenosis is unfavorably located at a bifurcation of the body part or blood vessel, the computing unit may suggest an additional third angulation, e.g., a further capture angle for a third X-ray capture.

Automatic analysis in the present case takes place on the assumption that the stenosis extends substantially parallel to the image plane of the first X-ray capture, e.g., the first capture angle has been made substantially perpendicular to the stenosis or the course thereof. On this basis, in the following evaluation act 10, the optimum second capture angle for the second X-ray capture may be assumed to be perpendicular to the center line 23 and to the first capture angle. In the present case, however, the computing unit verifies in parallel whether the optimum second capture angle is approachable and thus whether a second X-ray capture from the second capture angle is even possible. Further criteria may also be taken into account during evaluation, in the present case for example a degree of superposition of the specified body part by other parts which occur in accordance with a model stored in the computing unit.

The suitability of a plurality of specified further capture angles may accordingly be verified. Once a capture angle has been excluded, for example, because it is not approachable or fails to meet other minimum requirements, the further capture angle with the evaluation result may be set automatically by the computing unit. For example, capture angles falling below a specified minimum differential angle, (e.g., 40 degrees), between the two capture angles may be excluded from the set of possible second capture angles.

In the example shown, the computing unit then automatically selects the second capture angle for the second X-ray capture from a set of further capture angles. The selected angle is then displayed to an operator so that it may be set 11 in the next act. After setting 11, the second capture angle is approached 12 and the second X-ray capture is captured 13 from the approached second capture angle.

The second X-ray capture is automatically analyzed 14 in a further act. For example, the suitable frame with the cardiac phase of the frame selected from the first X-ray capture may be selected from the second X-ray capture. This may be done automatically without any problem because the cardiac phase for the frame from the first X-ray capture is already known to the doctor from the analysis 8 of the first X-ray capture. For example, the frame with the highest filling level of the body part, (e.g., the right coronary artery), with contrast agent may automatically be displayed from the frames with a suitable cardiac phase. The stenosis or the body part or vessel segment to be examined may also be automatically defined based on the epipolar lines known from the first X-ray capture. In an additional act, not shown here, the doctor may optionally also check once more whether the body part or vessel segment is detected without any superposition of other vessels and optionally make a correction such as a change in capture angle. Registration of the two X-ray captures to one another may also be considered as a correction at this point.

The next act is the generation 15 of the three-dimensional reconstruction of the body part, e.g., the right coronary artery. Once the three-dimensional reconstruction or model is known and thus the spatial position of the body part has been obtained, it is subsequently also possible to compare the actual capture angles with the optimum capture angles and in this manner to determine the quality of the X-ray captures and thus of the three-dimensional representation. This may be carried out for example automatically by matching the respective center lines in the X-ray captures or frames with the center line in the three-dimensional model. As a result, a spatially resolved quality of the three-dimensional reconstruction may be calculated as a function of the capture angles and output 16. The computing unit may optionally also suggest capturing a further X-ray capture with a suggestion for an optimum capture angle.

Figure 2:
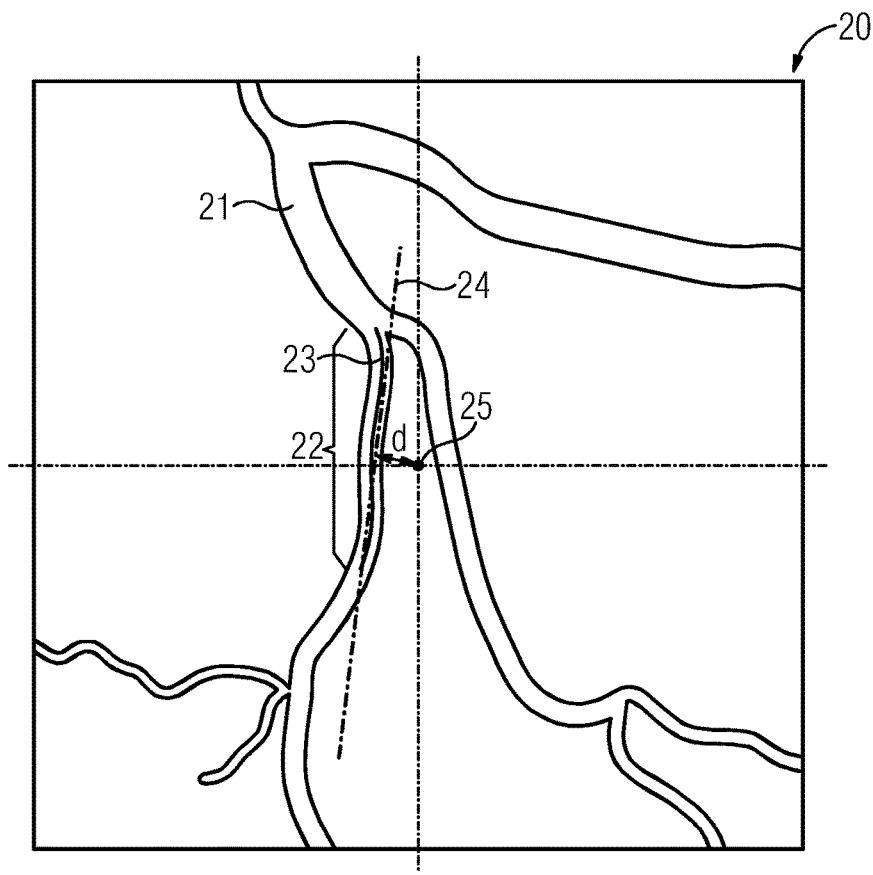
FIG. 2 depicts an exemplary first X-ray capture from a first capture angle for visualizing the analysis.

FIG. 2 depicts an exemplary first X-ray capture to illustrate the automatic analysis by the computing unit of a supplied X-ray capture. The first X-ray capture 20, square in the present example, in the present case shows a body part 21, (e.g., a blood vessel). In a region of the body part 21, a stenosis has now in the present case been detected in one region 22, either by an operator or by a computing unit. For purpose of automatic analysis 9 of the X-ray capture 20, a center line 23, which follows the course of the body part 21 affected by the stenosis in the region 22, is now automatically calculated. Using straightforward computing operations, a straight line may now be plotted through the center line 23. The straight line simultaneously serves as an axis of rotation 24, to which a normal of the image plane of a second X-ray capture, which serves for the generation of a three-dimensional reconstruction of the body part 21, may be perpendicular. A distance d from the center point 25 (e.g., isocenter) of the first X-ray capture may additionally be determined for the axis of rotation 24.

Figure 3:
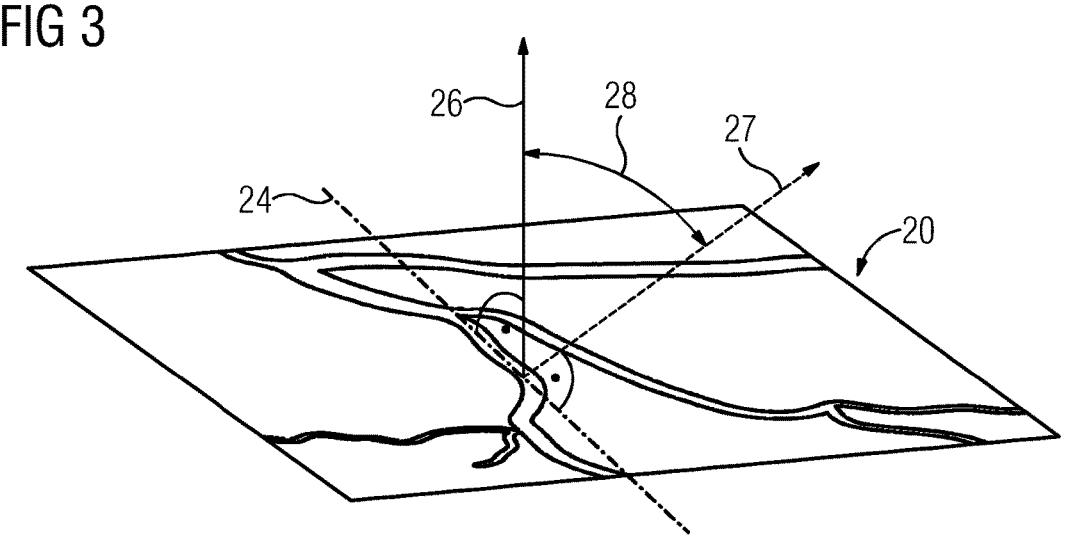
FIG. 3 depicts a schematic three-dimensional representation of the first X-ray image from FIG. 2 for visualizing the evaluation of the suitability of a further capture angle for the generation of the three-dimensional reconstruction.

FIG. 3 depicts a perspective view of the X-ray capture from FIG. 2. The normal vector 26 of the image plane of the X-ray capture 20 is additionally shown. The normal vector 27 of an image plane for the second X-ray capture may be tilted by a specified minimum differential angle relative to the normal 26. In the present case, the two image planes intersect at the axis of rotation 24. A differential angle 28 between the two normals 26, 27 thus also corresponds (with a minor correction, see below) to the difference between the first and the second capture angles. The differential angle 28 may amount to approx. 90°, (e.g., 90 degrees+/−10 degrees, or +/−5 degrees).

The differential angle 28 between the first and the second normals 26, 27 with regard to rotation about the axis of rotation 24 varies on rotation of the capture unit of the X-ray machine relative to the region 22 of the body part in a different manner than the capture angle itself. This is attributable to the fact that the region 22 may not be located at the image center point 25. Compensation is optionally necessary as a consequence. For example, as a function of the distance d of the axis of rotation 24 from the image center point 25, a compensating amount may be added to or subtracted from the differential angle 28.

Figure 4:
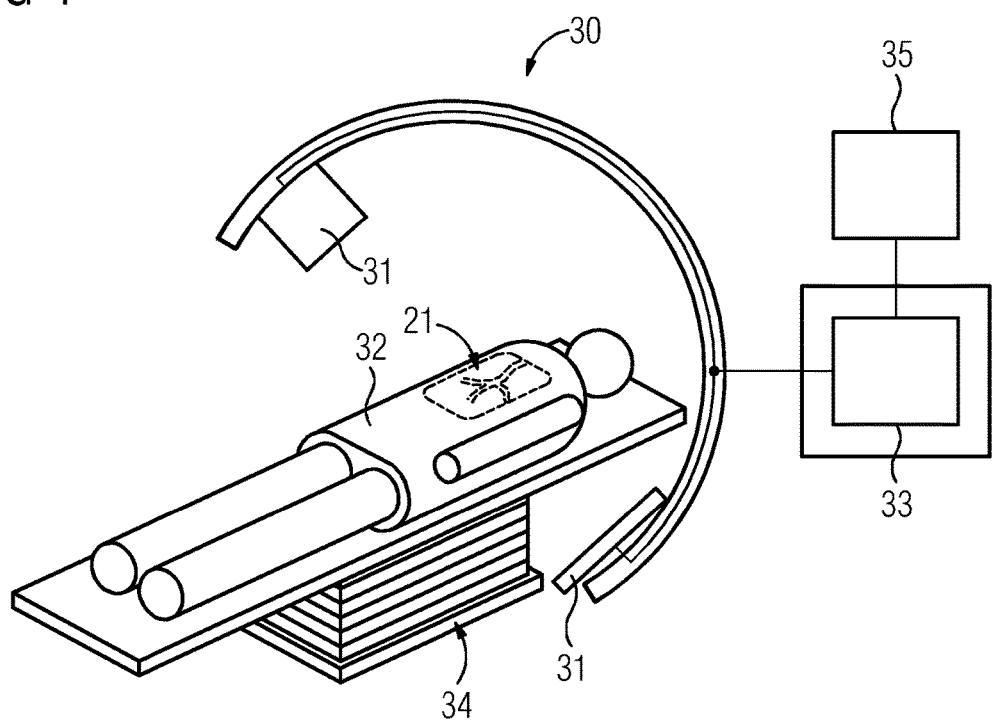
FIG. 4 depicts an exemplary embodiment of an X-ray machine.

FIG. 4 is a schematic representation of an exemplary embodiment. The X-ray machine 30 for the capture of at least two X-ray captures 20 (FIG. 2) for the generation of a three-dimensional reconstruction of a body part 21 includes a capture unit 31 for the capture of X-ray captures 20 from capture angles settable on the X-ray machine 30 and approachable by the capture unit 31 under manual control. The X-ray machine 30 also includes a computing unit 33 for the automatic analysis 9 of at least one first X-ray capture 20 supplied to the computing unit 33, which first X-ray capture is captured from a first capture angle, and for the evaluation 10 of the suitability of at least one further capture angle for the generation 15 of the three-dimensional reconstruction of the body part 21 in the light of a result from the automatic analysis 9. The X-ray machine 30 likewise includes a patient table 34 with an electrical adjustment function for a patient 32.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for an operation of an X-ray machine for generation of a three-dimensional reconstruction of a target portion of a body part, the method comprising:
supplying a first X-ray capture of the target portion of the body part, captured at a first capture angle, to a computing unit of the X-ray machine, wherein the body part comprises a portion of a blood vessel or an organ;
automatically analyzing the supplied first X-ray capture of the target portion of the body part by the computing unit, wherein a center line of the portion of the blood vessel or the organ is identified;
evaluating a suitability of at least one further capture angle, by the computing unit, based on the identified center line from the automatic analysis as an axis of rotation;
setting a second capture angle on the X-ray machine, with respect to a same target portion of the body part, either automatically by the computing unit, wherein a result from the evaluation is taken into account, or manually by an operator, wherein a result from the evaluation is displayed to the operator by a display unit of the X-ray machine, wherein the second capture angle is a different capture angle than the first capture angle;
controlling an approach to the set second capture angle using a capture unit of the X-ray machine about the axis of rotation;
capturing the second X-ray capture at the set second capture angle by the capture unit; and
generating the three-dimensional reconstruction of the same target portion of the body part using the first X-ray capture and the second X-ray capture.

2. The method of claim 1, further comprising:
selecting the generation of the three-dimensional reconstruction for the first X-ray capture from a plurality of options for captures by the X-ray machine;
automatically setting at least one capture parameter for the first X-ray capture;
setting the first capture angle;
controlling an approach to the set first capture angle using the capture unit of the X-ray machine; and
capturing the first X-ray capture at the set first capture angle by the capture unit.

3. The method of claim 2, wherein the selecting includes specifying the target portion of the body part to be reconstructed, and
wherein the setting of the first capture angle proceeds automatically.

4. The method of claim 2, wherein the capturing of the first X-ray capture having a plurality of individual images, the second X-ray capture having a plurality of individual images, or both the first and the second X-ray captures comprises automatic variation of the capture angle during capture of the first and/or second X-ray capture by less than 10 degrees.

5. The method of claim 1, wherein the automatic analysis comprises detection of the target portion of the body part, comprising one or more of at least one region of the body part with specified characteristics, a position of the body part, an orientation of the body part, at least one dimension of the body part, a course of the body part, or the axis of rotation about which the second X-ray capture is tilted relative to the first X-ray capture.

6. The method of claim 5, wherein the detection is of a region of the blood vessel, wherein the blood vessel has a stenosis.

7. The method of claim 1, wherein the evaluation of suitability includes one or more of the following criteria:
an angular difference between the first capture angle and the at least one further capture angle;
a probability of the X-ray machine colliding with a further item of equipment, the operator, a patient, or a combination thereof;
a dose burden for the patient;
approachability of the capture angle by the capture unit;
a path length of the X-rays in the patient; or
a number of further body parts superposed over the body part in the X-ray capture in accordance with a model.

8. The method of claim 1, wherein the evaluation of suitability takes account of at least one minimum requirement and, in the event of the at least one minimum requirement not being met by the evaluated capture angle, the computing unit prevents the evaluated capture angle from being set as the second capture angle and/or warns the operator in the event of the evaluated capture angle being set as the second capture angle.

9. The method of claim 8, wherein the at least one minimum requirement includes a specified angular amount by which the first and second capture angles differ.

10. The method of claim 1, wherein the X-ray machine comprises a patient table with an electrical adjustment function, the electrical adjustment function being disabled during capture of the first X-ray capture and/or the second X-ray capture, or
adjustment of the patient table is detected by a detection unit and taken into account during the setting of the second capture angle.

11. The method of claim 1, further comprising:
automatically preselecting correlated frames of the first and second X-ray captures by the computing unit based on the automatic analysis and/or of the evaluation of suitability for the generation of the three-dimensional reconstruction.

12. The method of claim 1, further comprising:
analyzing the second X-ray capture;
evaluating the suitability of at least one further capture angle for the generation of an improved three-dimensional reconstruction of the same target portion of the body part, by the computing unit, based on a result from the automatic analysis;
providing a third X-ray capture at a third capture angle, with respect to the same target portion of the body part, for the generation of the improved three-dimensional reconstruction;
setting a third capture angle on the X-ray machine;
controlling an approach to the set third capture angle using the capture unit of the X-ray machine; and
capturing the third X-ray capture at the set third capture angle using the capture unit for the generation of the improved three-dimensional reconstruction of the same target portion of the body part, wherein the third capture angle is a different capture angle than the first capture angle and the second capture angle.

13. An X-ray machine for capture of at least two X-ray images for generation of a three-dimensional reconstruction of a target portion of a body part, wherein the body part comprises a portion of a blood vessel or an organ, the X-ray machine comprising:
a capture unit; and
a computing unit configured to:
automatically analyze at least one first X-ray capture of the target portion of the body part supplied to the computing unit, wherein the first X-ray capture is captured at a first capture angle using the capture unit and wherein a center line of the portion of the blood vessel or the organ is identified, and
evaluate a suitability of at least one further capture angle for the generation of the three-dimensional reconstruction of a same target portion of the body part based on the identified center line from the automatic analysis as an axis of rotation,
wherein the capture unit is configured to capture a second X-ray capture at a second capture angle through a rotation of capture unit about the axis of rotation, with respect to the same target portion of the body part, for the generation of the three-dimensional reconstruction, wherein the second capture angle is a different capture angle than the first capture angle.

14. A method for an operation of an X-ray machine for generation of a three-dimensional reconstruction of a body part, the method comprising:
supplying a first X-ray capture of the body part, captured at a first capture angle, to a computing unit of the X-ray machine;
automatically analyzing the supplied first X-ray capture by the computing unit;
evaluating a suitability of at least one further capture angle, by the computing unit, based on a result from the automatic analysis, wherein the evaluation of suitability takes account of at least one minimum requirement comprising a specified angular amount by which the first capture angle and the at least one further capture angles differ;
setting a second capture angle on the X-ray machine when the at least one minimum requirement is met, either automatically by the computing unit, wherein a result from the evaluation is taken into account, or manually by an operator, wherein a result from the evaluation is displayed to the operator by a display unit of the X-ray machine;
controlling an approach to the set second capture angle using a capture unit of the X-ray machine; and
capturing the second X-ray capture at the set second capture angle by the capture unit for the generation of the three-dimensional reconstruction of the body part.

15. The method of claim 14, wherein the specified angular amount is 20 degrees, 30 degrees, or 40 degrees.

* * * * *